US009459183B1

(12) United States Patent
Schnakenberg et al.

(10) Patent No.: US 9,459,183 B1
(45) Date of Patent: Oct. 4, 2016

(54) SYSTEM FOR THE COLLECTION AND DISPOSAL OF GRAIN SAMPLES

(71) Applicants: Bruce D. Schnakenberg, Maxwell, NE (US); Matthew P. Jorgensen, North Platte, NE (US)

(72) Inventors: Bruce D. Schnakenberg, Maxwell, NE (US); Matthew P. Jorgensen, North Platte, NE (US)

( * ) Notice: Subject to any disclaimer, the term of this patent is extended or adjusted under 35 U.S.C. 154(b) by 153 days.

(21) Appl. No.: 14/597,636

(22) Filed: Jan. 15, 2015

(51) Int. Cl.
*B65G 53/14* (2006.01)
*G01N 1/04* (2006.01)

(52) U.S. Cl.
CPC .................................... *G01N 1/04* (2013.01)

(58) Field of Classification Search
CPC .................................................. B65G 53/14
USPC .................................. 406/38, 130, 151, 168
See application file for complete search history.

(56) References Cited

U.S. PATENT DOCUMENTS 4,341,492 A * 7/1982 Montgomery, Jr. ...... F04F 1/06 119/442
4,511,291 A * 4/1985 Quates, Sr. ............ B65G 53/14 406/128
5,118,225 A * 6/1992 Koch ..................... B65G 53/14 406/144
6,325,572 B1 * 12/2001 Dietrich ................. B65G 53/14 406/146
6,379,086 B1 * 4/2002 Goth ....................... B29C 47/10 406/130
6,443,669 B2 * 9/2002 Saito ............................ 198/390
6,994,497 B1 * 2/2006 Eriksson ................ B01J 8/0005 406/124
8,147,169 B1 * 4/2012 Kvalheim .............. B65G 53/40 406/109
8,882,401 B2 * 11/2014 Kinoshita .............. B65G 53/40 406/106
8,905,681 B2 * 12/2014 Schneider .............. B65G 53/06 209/139.1
2011/0047743 A1 * 3/2011 Shepherd ............... B65G 53/14 15/320
2016/0096693 A1 * 4/2016 Hanaoka ................ B65G 53/26 406/19
2016/0185538 A1 * 6/2016 Zinski .................... B65G 53/66 406/117

* cited by examiner

*Primary Examiner* — Joseph Dillon, Jr.
(74) *Attorney, Agent, or Firm* — Dennis L. Thomte; Thomte Patent Law Office LLC

(57) ABSTRACT

A system for the collection and disposal of grain samples including a grain sample receptacle, a vacuum bin and a vacuum pump. A grain sample conduit extends from a discharge opening of the receptacle to the upper interior of the vacuum bin. The air inlet end of the vacuum pump is connected to the interior of the vacuum bin to create a negative pressure therein. The grain samples which have been tested are dumped into the receptacle. When the receptacle is full, the vacuum pump is operated so that the grain samples in the receptacle will be drawn into the interior of the vacuum bin. When the vacuum bin is full, the vacuum bin may be transported to a dump pit or the like so that the contents of the vacuum bin may be dumped therefrom into the dump pit.

10 Claims, 10 Drawing Sheets

SYSTEM FOR THE COLLECTION AND DISPOSAL OF GRAIN SAMPLES

BACKGROUND OF THE INVENTION

1. Field of the Invention

This invention relates to a system for the collection and disposal of grain samples which have been tested at a grain testing station and more particularly to a system of the type described for use at a grain elevator or the like wherein a large number of grain samples are tested as grain is being delivered to the elevator or the like.

2. Description of the Related Art

At grain receiving businesses such as grain elevators or the like, the grain in each truckload is usually sampled and tested. The grain may be tested for moisture content, FM, splits, oils, proteins, Aflo, Uomi, insects, heat damage, odor, etc. After the sample has been tested, the sample and the excess grain associated therewith are usually placed in a trash can or bucket which requires manual emptying. The filled trash cans or buckets are very heavy and may cause back injuries to persons emptying the trash cans or buckets.

SUMMARY OF THE INVENTION

This Summary is provided to introduce a selection of concepts in a simplified form that are further described below in the Detailed Description. This Summary is not intended to identify key aspects or essential aspects of the claimed subject matter. Moreover, this Summary is not intended for use as an aid in determining the scope of the claimed subject matter.

A system is disclosed for the collection and disposal of grain samples which have been tested at a grain testing station or facility. The grain may be tested for moisture content, FM, splits, oils, proteins, Aflo, Uomi, insects, heat damage, odor, etc. The system includes an upstanding grain sample receptacle at the grain testing station with the grain sample receptacle having a lower end, upstanding side walls, an open upper end, and a bottom wall positioned above the lower end thereof which define an interior sample collection compartment for receiving grain samples therein which have been tested and the excess grain associated with the samples. The bottom wall of the grain sample receptacle has a discharge opening formed therein. The system also includes a grain sample conduit having an inlet end and a discharge end. The inlet end of the grain sample conduit is in communication with the discharge opening in the bottom wall of the grain sample receptacle. The grain sample receptacle has a valve member configured to selectively and adjustably close the discharge opening in the bottom wall thereof.

The system also includes an upstanding vacuum bin remote from the grain sample receptacle. The vacuum bin has a bottom wall, upstanding side walls, and a closed upper end which define a grain sample collection chamber therein. The bottom wall of the vacuum bin has one or more selectively closable discharge openings formed therein.

The discharge end of the grain sample conduit is in communication with the grain sample collection chamber adjacent the closed upper end of the vacuum bin. The system further includes a vacuum pump having an air inlet end and an air discharge end. A vacuum conduit extends between the air inlet opening of the vacuum pump and the interior of the grain collection chamber of the vacuum bin whereby the vacuum pump is configured to create a negative vacuum pressure in the grain sample collection chamber of the vacuum bin so that grain samples and excess grain in the interior sample collection compartment of the grain sample receptacle will be drawn therefrom into the grain sample conduit and thence into the grain sample collection chamber in the vacuum bin.

The lower end of the vacuum bin has a pair of spaced-apart tine tubes formed therein which are adapted to receive the tines of a fork lift or the like so that the vacuum bin may be moved to a disposal area and the material therein dumped through the discharge opening or openings in the bottom wall of the vacuum bin.

It is therefore a principal object of the invention to provide a system for the collection and disposal of grain samples which have been tested at a grain testing station.

A further object of the invention is to provide a system of the type described which enables the collection and disposal of grain samples which have been tested and the excess grain associated therewith.

A further object of the invention is to provide a system of the type described which eliminates the need for manually lifting buckets or containers of spent grain samples and any excess grain associated therewith.

A further object of the invention is to provide a unique system which is economical of manufacture, durable in use and refined in appearance.

These and other objects will be apparent to those skilled in the art.

BRIEF DESCRIPTION OF THE DRAWINGS

Non-limiting and non-exhaustive embodiments of the present invention are described with reference to the following figures, wherein like reference numerals refer to like parts throughout the various views unless otherwise specified.

DESCRIPTION OF THE PREFERRED EMBODIMENT

Figure 1:
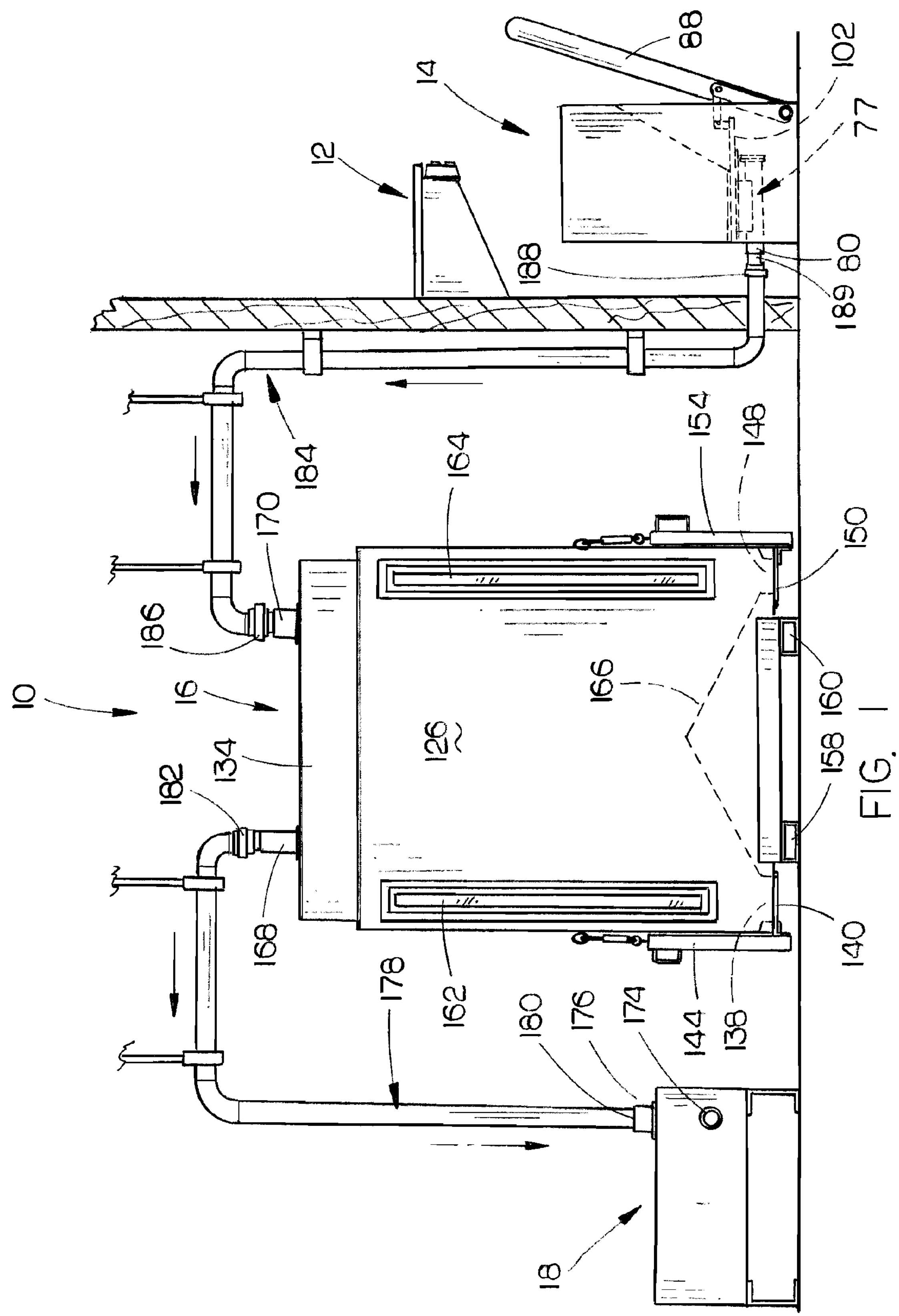
FIG. 1 is a front elevational view of the system of this invention.
Figure 2:
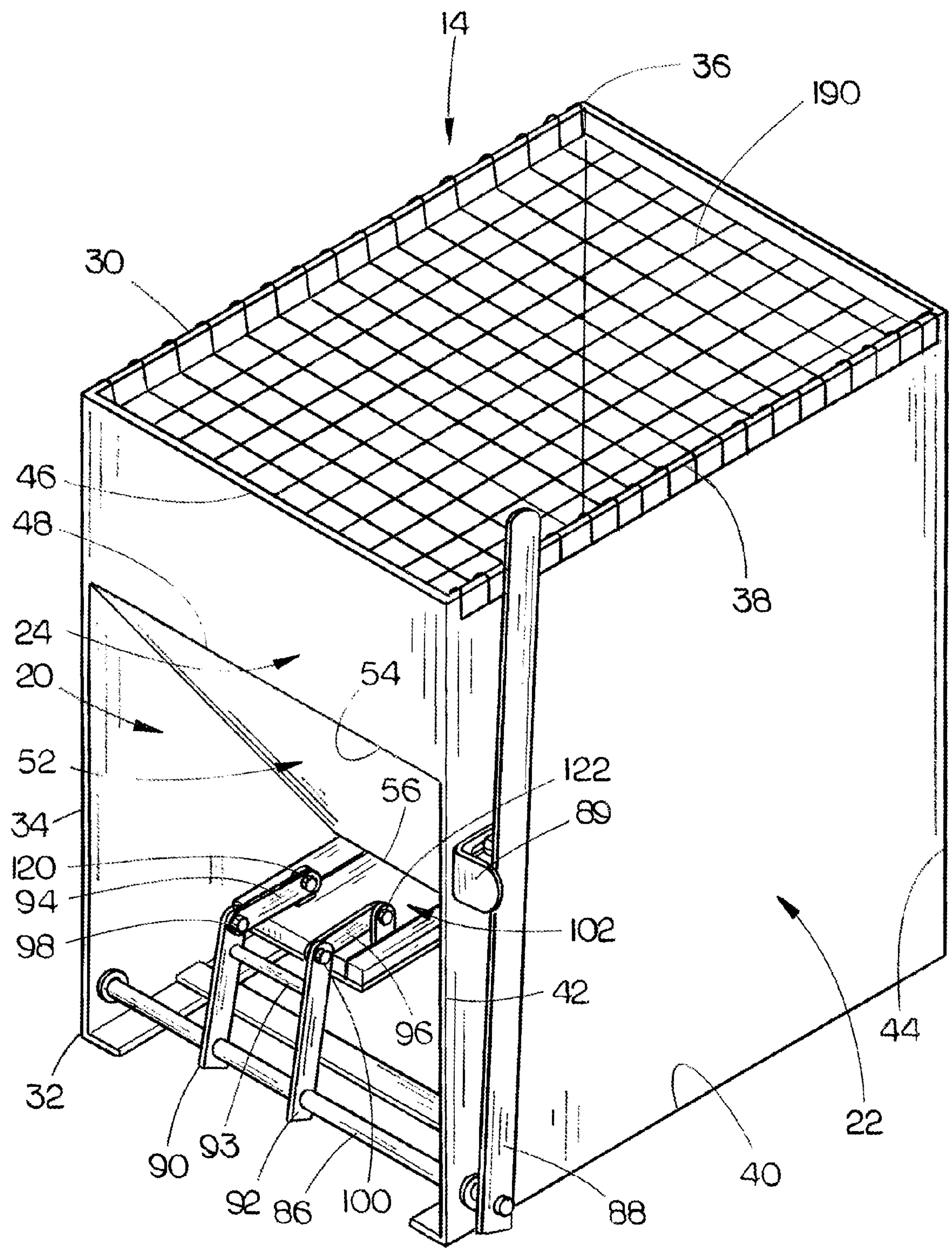
FIG. 2 is a front perspective view of the grain sample receptacle of this invention.
Figure 3:
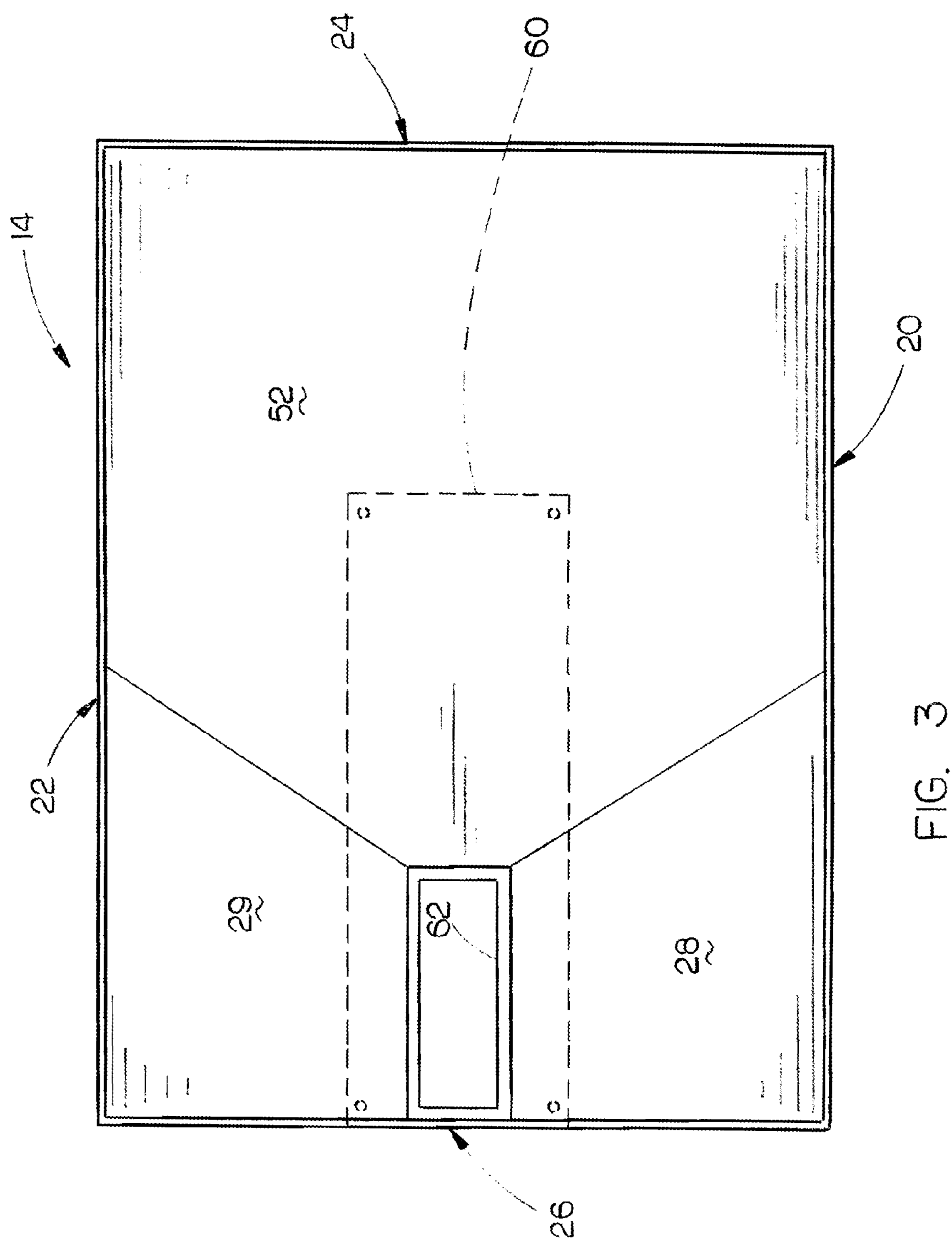
FIG. 3 is a top elevational view of the grain sample receptacle of this invention.
Figure 4:
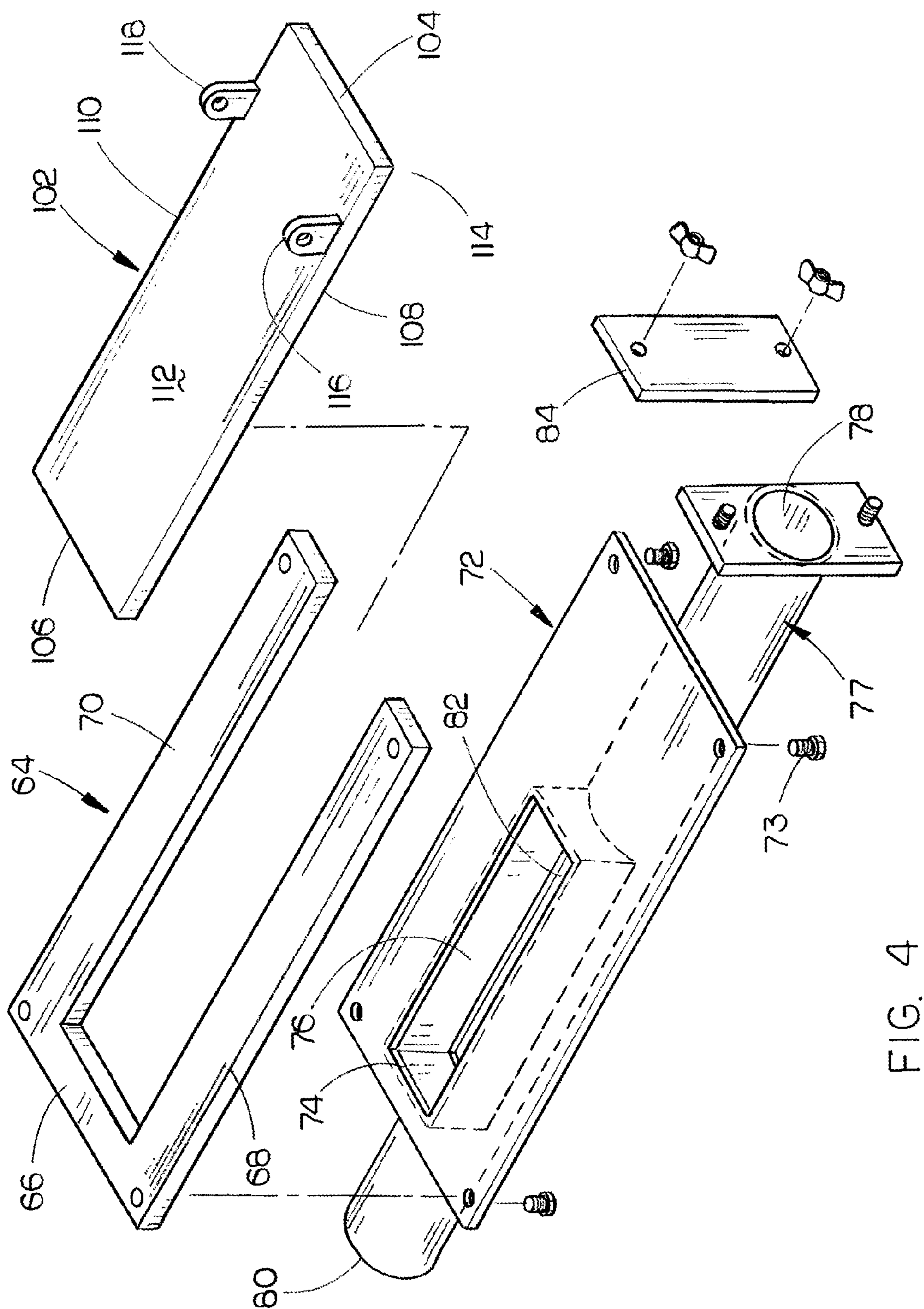
FIG. 4 is an exploded perspective view of a portion of the grain sample receptacle of this invention.
Figure 5:
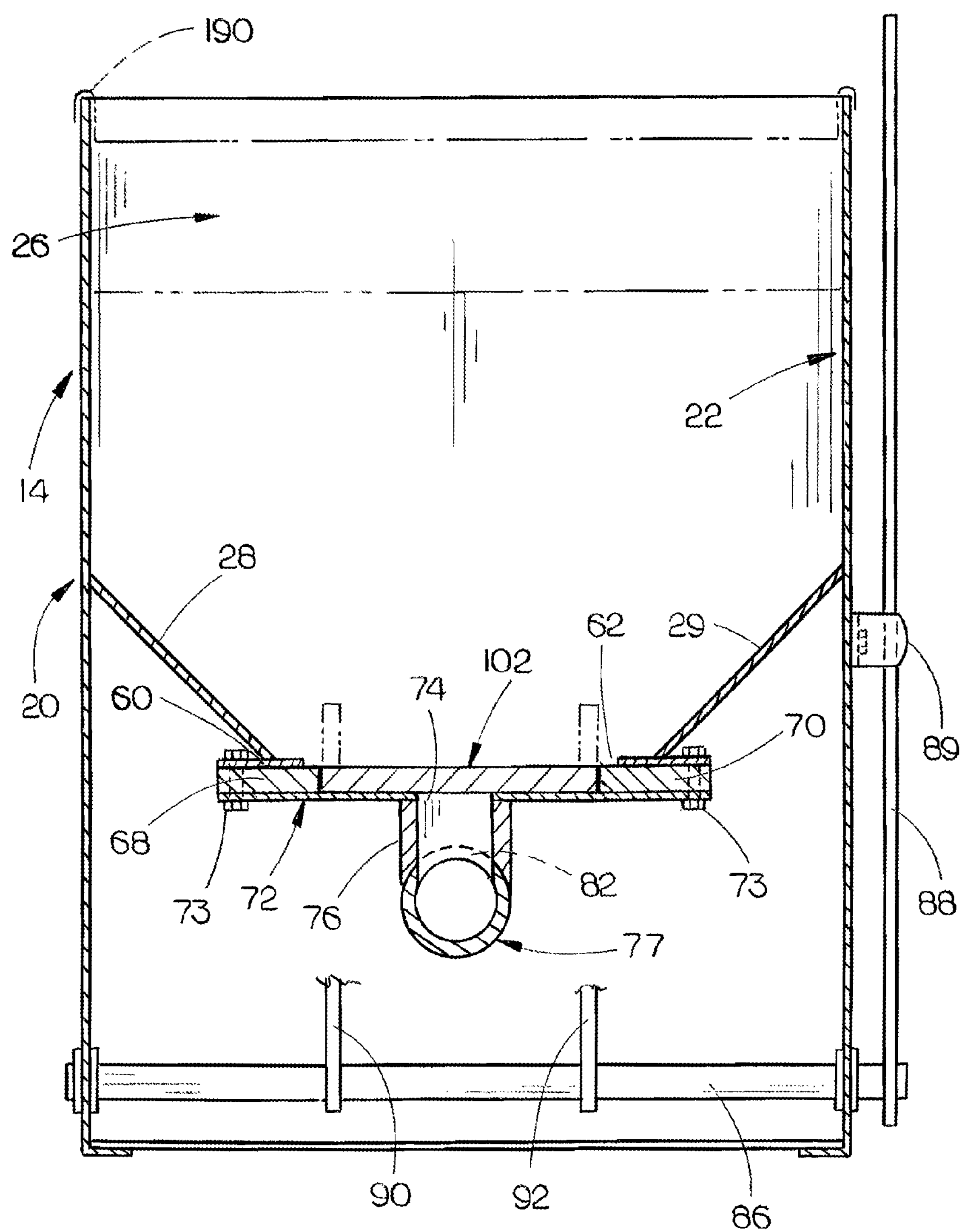
FIG. 5 is a partial sectional view of the grain sample receptacle of this invention.
Figure 6:
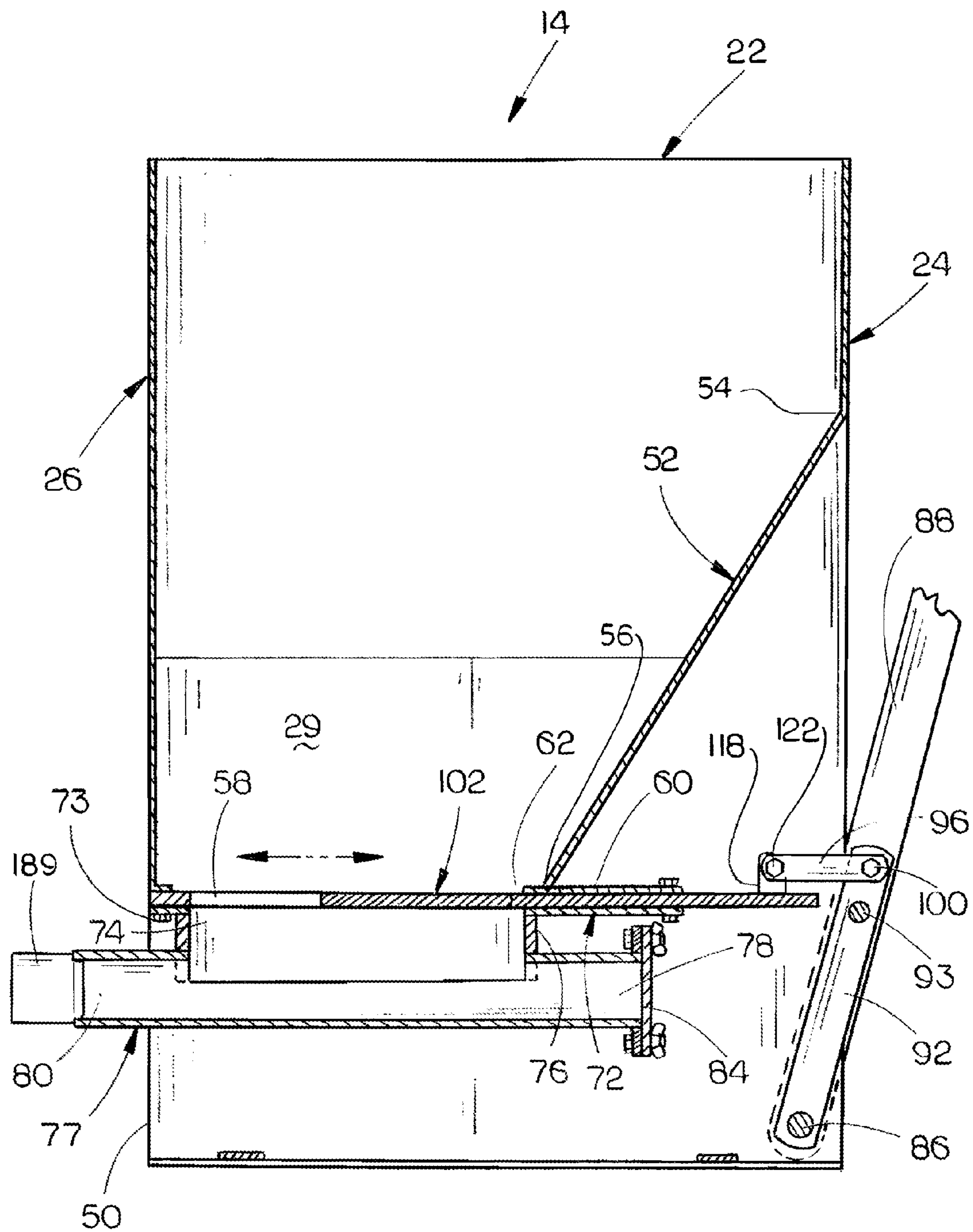
FIG. 6 is a partial sectional view of the grain sample receptacle of this invention.
Figure 7:
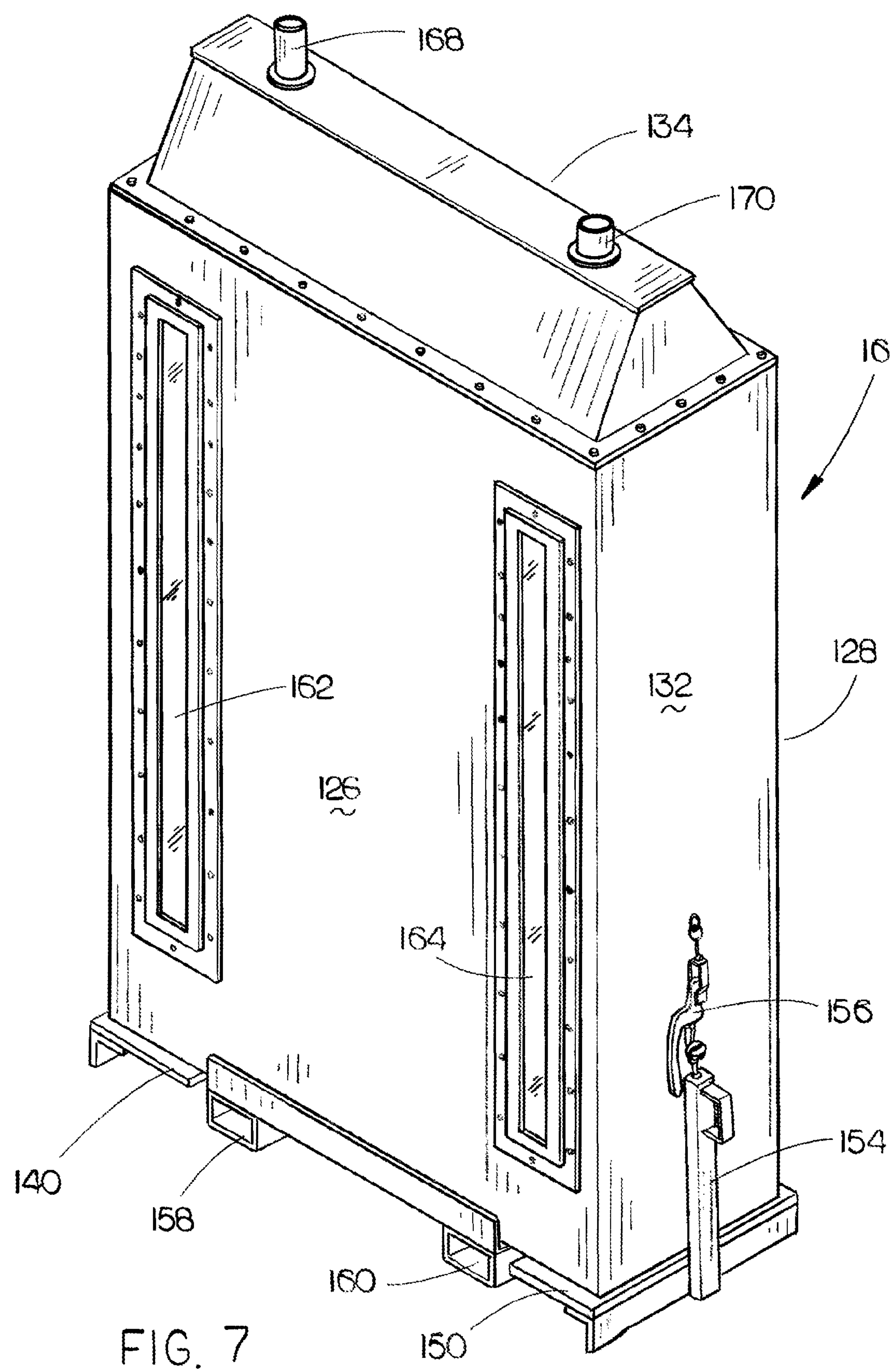
FIG. 7 is a front perspective view of the vacuum bin of this invention.
Figure 8:
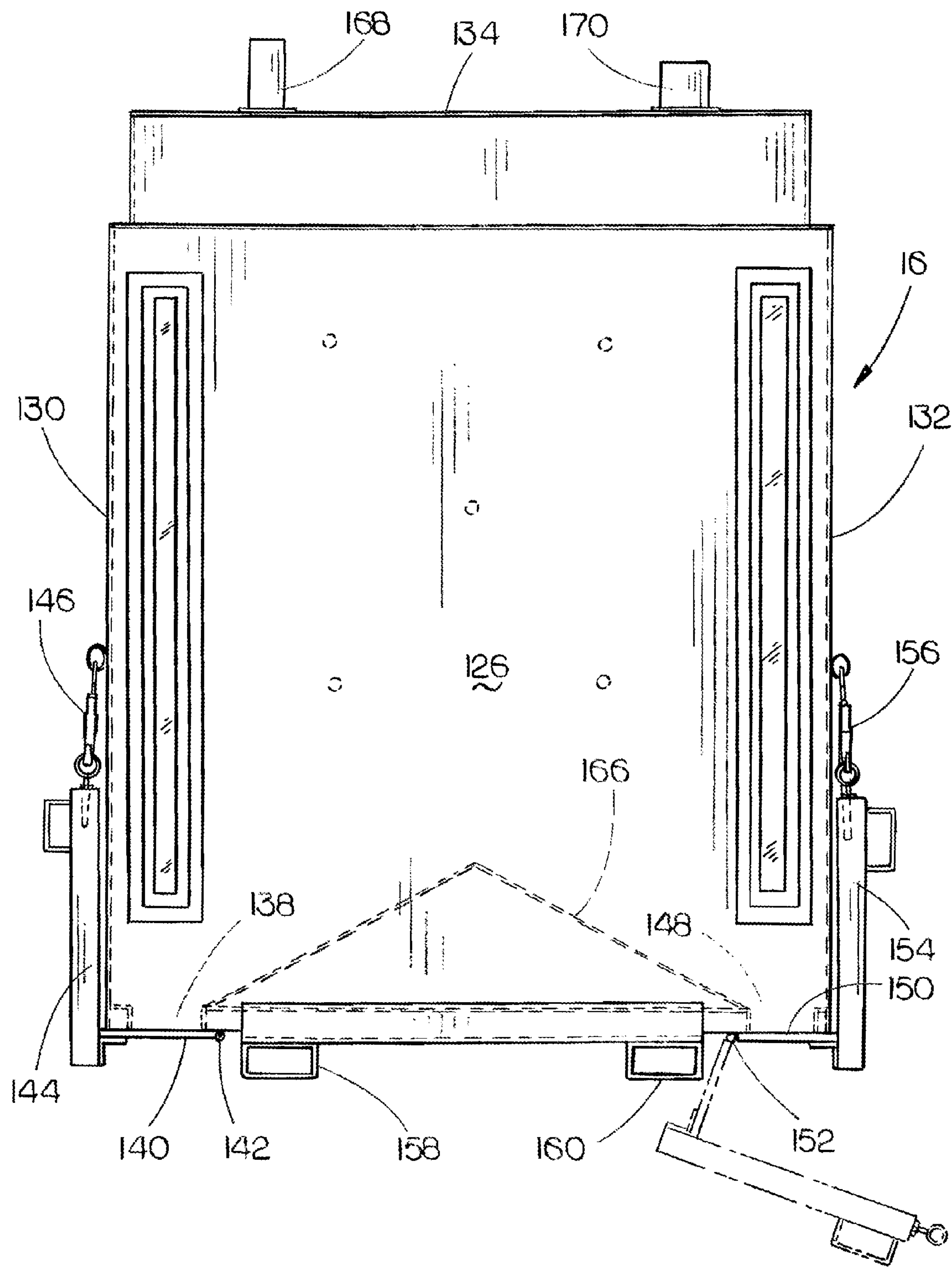
FIG. 8 is a front elevational view of the vacuum bin of this invention.
Figure 9:
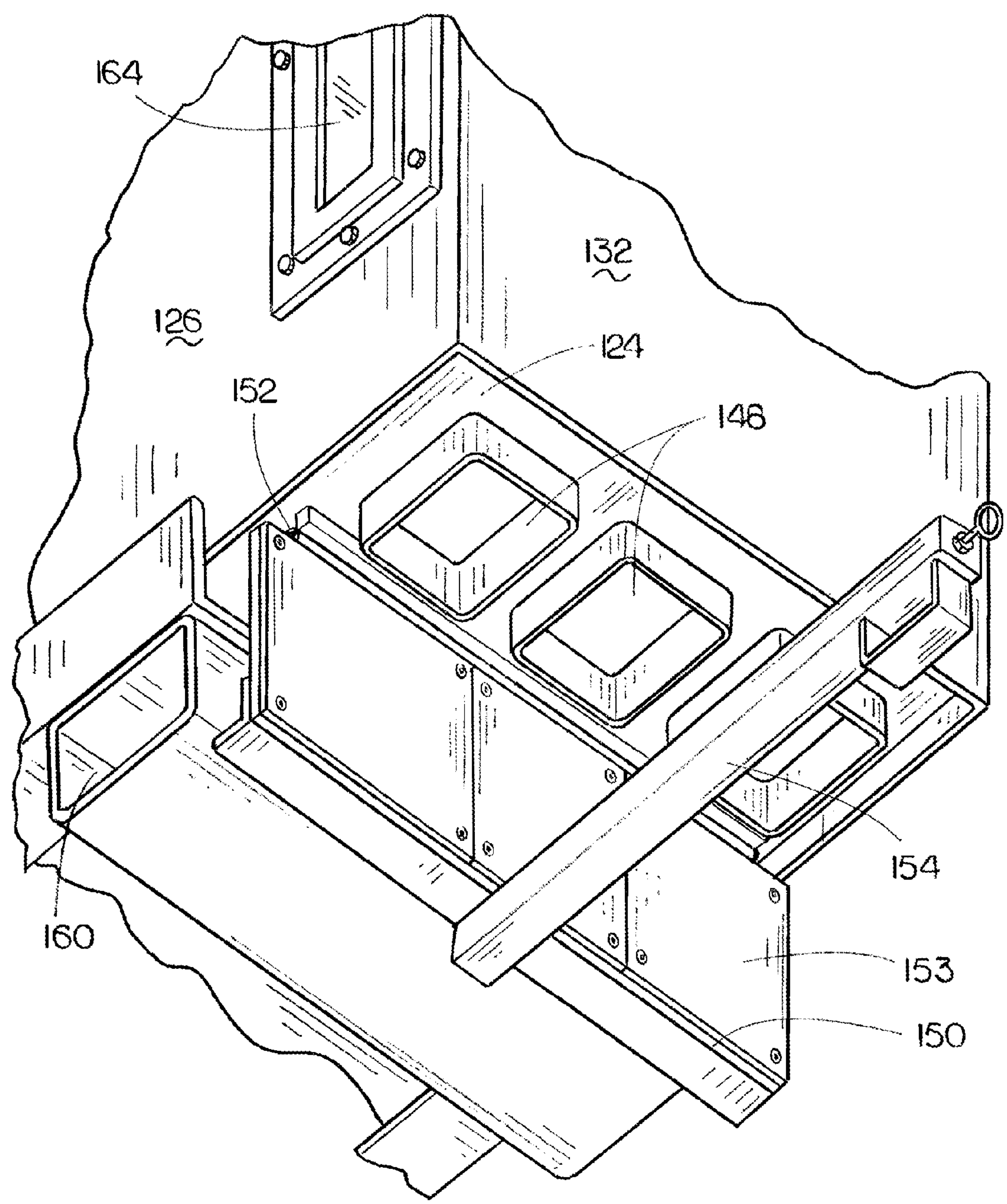
FIG. 9 is a partial bottom perspective view of the vacuum bin of this invention.
Figure 10:
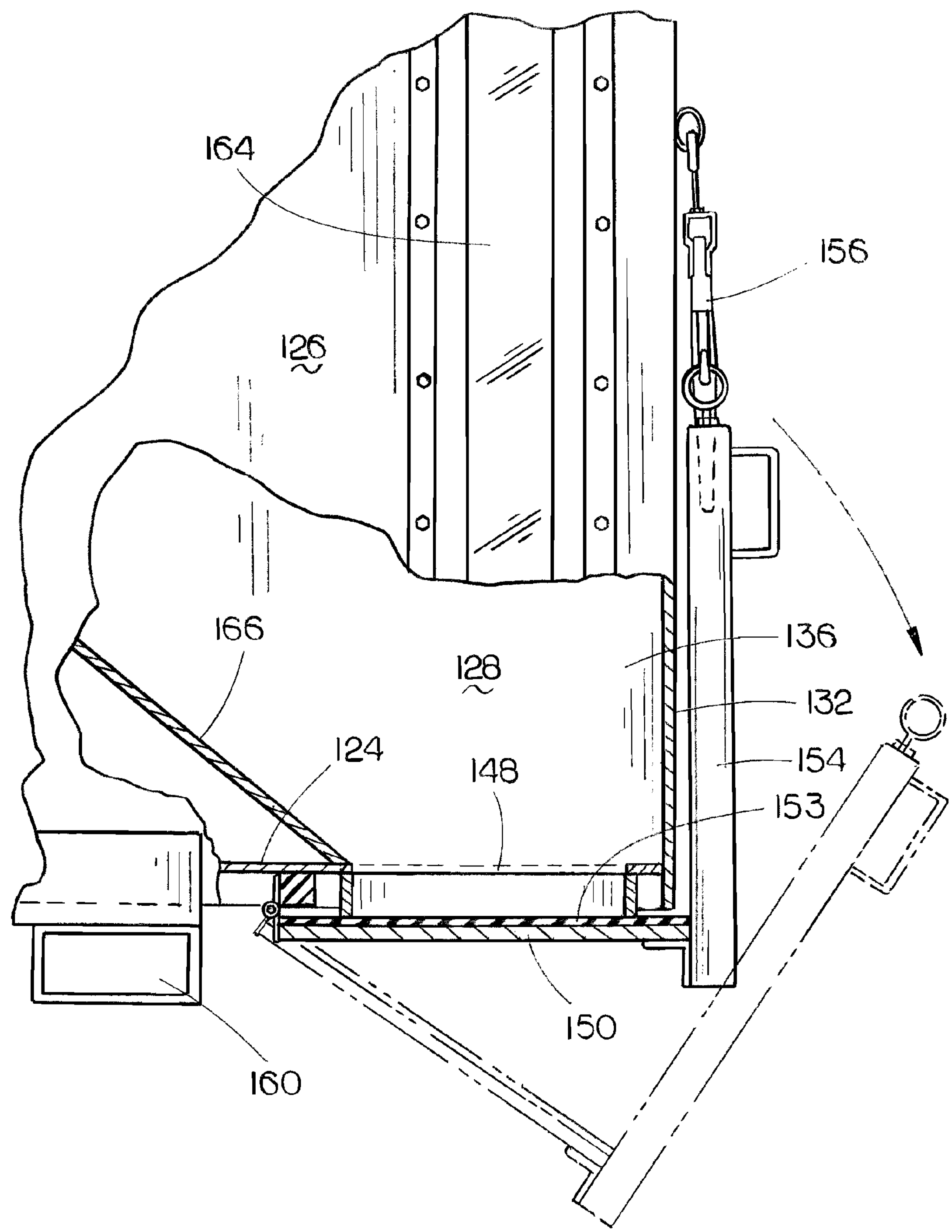
FIG. 10 is a partial front elevational view of the vacuum bin of this invention with portions thereof cut away to more fully illustrate the vacuum bin of this invention.

Embodiments are described more fully below with reference to the accompanying figures, which form a part hereof and show, by way of illustration, specific exemplary embodiments. These embodiments are disclosed in sufficient detail to enable those skilled in the art to practice the invention. However, embodiments may be implemented in many different forms and should not be construed as being limited to the embodiments set forth herein. The following detailed description is, therefore, not to be taken in a limiting sense in that the scope of the present invention is defined only by the appended claims.

The numeral 10 refers to the system of this invention for the collection and disposal of grain samples which have been tested at a grain testing station 12 at a grain receiving facility such as a grain elevator or the like. The system 10 not only collects and disposes of the spent grain samples but also collects and disposes of the excess grain associated with the grain samples.

System 10 is comprised of three main components; namely, a grain sample receptacle 14, a vacuum bin 16 and a vacuum pump 18. The receptacle 14 will usually be located in the room where the grain sample is tested. The vacuum bin 16 will usually be located some distance from the receptacle 14 so that a vehicle such as a fork lift may lift the vacuum bin from its supporting surface and move the vacuum bin to a dump pit or the like. Vacuum pump 18 may be located near the vacuum bin or may be located some distance therefrom.

Receptacle 14 will be described as having vertically disposed side walls 20 and 22, a vertically disposed front wall portion 24, a vertically disposed back wall portion 26, and inwardly and downwardly sloped bottom wall members 28 and 29. Side wall 20 has an upper end 30, a lower end 32, a front end 34 and a back end 36. Side wall 22 has an upper end 38, a lower end 40, a front end 42 and a back end 44. Front wall portion 24 is secured to and extends between side walls 20 and 22 at the upper ends thereof and has an upper end 46 and a lower end 48. As seen, the lower end 48 of front wall portion 24 is spaced above the lower ends of side walls 20 and 22. As also seen, the back wall portion 26 has an access opening 50 formed therein which extends upwardly thereinto from the lower end thereof.

An inclined wall portion 52, having an upper end 54 and a lower end 56, is secured to the inner surfaces of side walls 20 and 22 and extends downwardly and inwardly from the inside surface of front wall portion 24 into the receptacle 14. Wall member 28 extends downwardly and inwardly from the inner side of side wall 20 between back wall portion 26 and the inclined wall portion 52. Wall member 29 extends downwardly and inwardly from the inner side of side wall 22 between back wall portion 26 and the inclined wall portion 50. The lower ends of wall members 28 and 29 are spaced-apart to form a rectangular and horizontally disposed discharge opening 58 therebetween.

A rectangular flat plate 60 is positioned below discharge opening 58 and is welded to the underside of the lower ends of wall members 28, 29 and inclined wall portion 52. Plate 60 has a rectangular discharge opening 62 formed therein which registers with discharge opening 58. The length and width of discharge opening 62 is slightly less than the length and width of discharge opening 58 so that the edges of discharge opening 62 protrude inwardly from the edges of the discharge opening 58.

The numeral 64 refers to a horizontally disposed valve body which is secured to the underside of plate 60 by bolts 65. Valve body 64 includes a base portion 66 which is transversely disposed with respect to the longitudinal axes of discharge openings 58 and 62 and which is spaced rearwardly of openings 58 and 62. A leg portion 68 extends transversely from one end of base portion 66 towards the front of receptacle 14 and which is spaced laterally from one side of discharge openings 58 and 62. A leg portion 70 extends transversely from the other end of base portion 66 towards the front of receptacle 14 and which is positioned laterally outwardly from the other side edges of discharge openings 58 and 62. A flat plate 72 is secured to the undersides of base portion 66, leg portion 68 and leg portion 70 so as to extend therebetween.

Plate 72 has a rectangular discharge opening 74 formed in plate 72 which registers with discharge opening 62 in plate 60. A rectangular hollow housing 76 is secured to the underside of plate 72 so as to register with opening 74 of plate 72. An elongated and horizontally disposed tube 77, having ends 78 and 80, is welded to the underside of plate 72 and has an elongated intake opening 82 formed in the upper end thereof which registers with discharge opening 74. End 78 of tube 77 is selectively closed by a cover 84. The end 80 is open as will be described in more detail hereinafter.

The numeral 86 refers to an elongated shaft having its ends rotatably mounted in the lower ends of side walls 20 and 22 at the lower front ends thereof. One end of shaft 86 extends outwardly from side wall 22 and has the lower end of a handle 88 fixedly secured thereto. Handle 88 could be secured to the other end of shaft 86 if so desired. The numeral 89 refers to a stop which is adjustably secured to the outer side of wall 22 which is in the pivotal path of handle 88. Stop 89 will be adjusted to maintain the valve plate 102 in a partially open position to accommodate various grain sizes. A pair of elongated links 90 and 92 have their lower ends welded to shaft 86 for pivotal movement therewith. A pair of elongated links 94 and 96 have their forward ends pivotally secured to the upper ends of links 90 and 92 respectively by bolts 98 and 100 respectively. The numeral 102 refers to a generally flat valve plate having a forward end 104, a rearward end 106, a first side 108, a second side 110, an upper surface 112 and a lower surface 114. A pair of upstanding brackets 116 and 118 are secured to valve plate 102 adjacent sides 108 and 110 respectively. The forward ends of links 94 and 96 are pivotally secured to brackets 116 and 118 respectively by bolts 120 and 122 respectively. Valve plate 102 is slidably received between leg portions 68 and 70 of valve body 64 and plates 60 and 72 and is selectively slidably movable between inner and outer positions with respect thereto, as will be described in detail hereinafter.

The vacuum bin 16 includes a bottom wall 124 an upstanding front wall 126, an upstanding back wall 128, side walls 130 and 132, and an upper wall 134, which define a sample collection chamber 136. Bottom wall 124 has a plurality of discharge openings 138 formed therein adjacent side wall 130 which communicate with chamber 136. A flat rectangular gate 140 is pivotally or hingedly secured to bottom wall 124 at 142 and is movable between open and closed positions. In its closed position, gate 140 closes the discharge openings 138. A handle 144 is secured to gate 140 for moving gate 140 between its open and closed positions. A locking mechanism 146 is secured to handle 144 to hold handle 144 adjacent the outer side of side wall 130 to maintain gate 140 in its closed position.

Bottom wall 124 has a plurality of discharge openings 148 formed therein adjacent side wall 132 which communicate with chamber 136. A flat rectangular gate 150 is pivotally or hingedly secured to bottom wall 124 at 152 and is movable between open and closed positions. In its closed position, gate 150 closes the discharge openings 148. A urethane material 153 is secured to the upper surface of gate 150. A handle 154 is secured to gate 150 for moving gate 150 between its open and closed positions. A locking mechanism 156 is secured to handle 154 to hold handle 154 adjacent the outer side of side wall 132 to maintain gate 150 in its closed position.

Fork lift tine tubes 158 and 160 are secured to the underside of bottom wall 124 inwardly of discharge openings 138 and 148 respectively so that a fork lift vehicle may insert the tines thereof into the tubes 158 and 160 to move the vacuum bin 16 which will normally be located remotely of the receptacle 14.

The front wall 126 of vacuum bin 16 has a pair of sight glasses 162 and 164 formed therein to enable a person to observe the level of grain samples therein. An inclined baffle 166 is provided in chamber 136 at the lower end thereof to direct the samples therein to the discharge openings 138 and 148. A quick connector coupling member 168 is secured to upper wall 134 with the upper end thereof being positioned above upper wall 134 and its lower end being in communication with the interior of chamber 136. A quick-connector coupling member 170 is secured to upper wall 134 with the upper end thereof being positioned above upper wall 134 and its lower end being in communication with the interior of chamber 136. Preferably, member 168 is larger in size than member 170. The vacuum bin 16 may have a pressure switch provided therein which will be activated when the grain in the vacuum bin reaches a predetermined level. The pressure switch could be connected to a light in the area in which the receptacle 14 is located to alert the operator that the bin 116 is full.

The conventional vacuum pump 18 may be located near the vacuum bin 16 or remote therefrom. Vacuum pump 16 has an air discharge end 174 and an air inlet end 176. The numeral 178 refers to a vacuum base or conduit having air discharge end 180 which is connected to the air inlet end 176. The numeral 178 refers to a vacuum base or conduit having air discharge end 180 which is connected to the air inlet end 176 of vacuum pump 172. Vacuum conduit 178 has an air inlet end 182 which is selectively removably coupled to the coupler 168. An elongated sample conduit 184 has its discharge end 186 selectively removably coupled to the coupling 170. The inlet end 188 of conduit 184 is selectively removably coupled to the end 78 of tube 77. If needed, a venturi 189 may be positioned between the end 78 of tube 77 and the inlet end of conduit 184.

The system 10 functions as will now be described. A screen 190 is preferably positioned on the upper end of receptacle 14 to prevent large excess grain particles or cobs from passing downwardly into the receptacle 14. The tested samples and excess grain is deposited into the receptacle 14. Initially, the vacuum plate will be in its closed position and the vacuum pump will not be running. When the samples reach a predetermined level in the receptacle as visually determined by a light, the operator will adjustably open the discharge opening 58 by pivotally moving handle 88 towards the front of receptacle 14 which opens discharge opening 58 to permit the grain samples to pass downwardly into tube 77. The stop 89 will have been previously adjusted to maintain handle 88 in a predetermined position so that the discharge opening 58 is open to a predetermined amount. Prior to opening the valve plate, the vacuum pump 18 will usually be activated to create a negative vacuum pressure in vacuum bin 16. The negative pressure in vacuum 16 will draw or suck the grain samples in tube 77 therefrom into the inlet end of sample conduit and into the sample collection chamber 136 of vacuum bin 16 to empty the receptacle 14.

When the vacuum bin 16 is full, the vacuum pump 18 will be turned off. The coupling 170 will be disconnected from the discharge end 186 of sample conduit 184 and the coupling 168 will be disconnected from the conduit 176. A fork lift truck or vehicle will then insert its tines into the tubes 158 and 160 and transfer the vacuum bin 16 to a dump pit or the like. The gates 140 and 150 will then be opened to permit the contents of the vacuum bin 16 to be dumped therefrom.

Thus it can be seen that the invention accomplishes at least all of its stated objectives.

Although the invention has been described in language that is specific to certain structures and methodological steps, it is to be understood that the invention defined in the appended claims is not necessarily limited to the specific structures and/or steps described. Rather, the specific aspects and steps are described as forms of implementing the claimed invention. Since many embodiments of the invention can be practiced without departing from the spirit and scope of the invention, the invention resides in the claims hereinafter appended.

We claim:

1. A system for the collection and disposal of grain samples which have been tested at a grain testing station, comprising:

an upstanding grain sample receptacle at the grain testing station with the grain sample receptacle having a lower end, upstanding side walls, an open upper end, and a bottom wall positioned above said lower end thereof which define an interior sample collection compartment for receiving grain samples therein which have been tested;

said bottom wall having a discharge opening formed therein;

a grain sample conduit having an inlet end and a discharge end;

said inlet end of said grain sample conduit being in operative communication with said discharge opening in said bottom wall of said grain sample receptacle;

said grain sample receptacle having a selectively movable valve member configured to selectively and adjustable close said discharge opening in said bottom wall thereof;

an upstanding vacuum bin remote from said grain sample receptacle;

said vacuum bin having a bottom wall, upstanding side walls, and a closed upper end which define a grain sample collection chamber;

said bottom wall of said vacuum bin having at least one normally closed discharge opening formed therein;

said discharge end of said grain sample conduit being in communication with said grain sample collection chamber adjacent said closed upper end of said vacuum bin;

a vacuum pump having an air inlet end and an air discharge end;

and a vacuum conduit extending between said air inlet end of said vacuum pump and the interior of said grain collection chamber of said vacuum bin with said vacuum pump being configured to selectively create a negative vacuum pressure in said grain sample collection chamber of said vacuum bin so that grain samples in said interior collection compartment of said grain sample receptacle will be drawn therefrom into said grain sample conduit and thence into said grain sample collection chamber in said vacuum bin;

said vacuum bin having a pair of fork lift tine receiving tubes secured thereto whereby said vacuum bin may be moved to a location for the disposal of the grain samples in said grain sample collection chamber through the at least one discharge opening in said bottom wall thereof.

2. The system of claim 1 wherein said grain sample conduit extends into said grain sample receptacle adjacent said lower end thereof and wherein said grain sample receptacle has an inclined wall therein which directs grain samples towards said inlet end of said grain sample conduit.

3. The system of claim 1 wherein said vacuum bin has at least one vertically disposed sight glass in one of said side walls therein so that the level of grain samples in said vacuum bin is visible.

4. The system of claim 1 wherein said discharge end of said grain sample conduit is selectively removably secured to said vacuum bin and wherein said air inlet end of said vacuum conduit is selectively removably secured to said vacuum bin.

5. The system of claim 1 further including a perforated screen member which is positioned over said open upper end of said grain sample receptacle.

6. The system of claim 1 wherein first and second spaced-apart discharge openings are formed in said bottom wall of said vacuum bin and wherein first and second gates are pivotally secured to said vacuum bin for the selective closure of said first and second discharge openings respectively.

7. The system of claim 6 wherein an elongated handle is secured to each of said first and second gates for pivotally moving the associated gate between open and closed positions.

8. The system of claim 7 wherein structure is provided for locking each of said handles in a position to maintain the associated gate in its closed position.

9. The system of claim 1 wherein a handle is secured to said valve of said grain sample receptacle for the selective movement of said valve between open and closed positions and positions therebetween.

10. The system of claim 9 wherein an adjustable stop is provided for maintaining said handle in a predetermined position.

* * * * *